United States Patent [19]
Guadagni et al.

[11] 4,031,265
[45] June 21, 1977

[54] METHOD OF REDUCING BITTERNESS IN CITRUS JUICES

[75] Inventors: Dante G. Guadagni, Moraga; Robert M. Horowitz, Pasadena; Bruno Gentili, Glendale; Vincent P. Maier, Newport Beach, all of Calif.

[73] Assignee: The United States of America as represented by the Secretary of Agriculture, Washington, D.C.

[22] Filed: June 18, 1975

[21] Appl. No.: 587,922

[52] U.S. Cl. .................................. 426/599; 426/616
[51] Int. Cl.² ...................... A23L 2/02; A23L 2/26

[58] Field of Search ............. 426/599, 534, 51, 616

[56] References Cited
OTHER PUBLICATIONS

Journal of Agricultural & Food Chemistry, v17, p. 698, 1969, Horowitz.

*Primary Examiner*—Hiram H. Bernstein
*Attorney, Agent, or Firm*—M. Howard Silverstein; David G. McConnell

[57] ABSTRACT

Bitterness in citrus juices is reduced by addition of a minor proportion of neodiosmin.

4 Claims, No Drawings

METHOD OF REDUCING BITTERNESS IN CITRUS JUICES

DESCRIPTION OF THE INVENTION

This invention relates to and has among its objects the reduction of bitterness in citrus juices. Further objects of the invention will be evident from the following description wherein parts and percentages are by weight unless otherwise specified. The abbreviation "ppm" used herein refers to parts per million.

In the following description, the application of the invention to navel orange juice is stressed. It should be understood that this particular embodiment of the invention is provided by way of illustration and not limitation. In its broad ambit the invention is applicable to juices from all kinds of citrus fruits including oranges, lemons, grapefruit, tangerines, mandarins, limes, tangelos, citrus hybrids, and the like. Furthermore, although the emphasis in this description is on application of of the invention to citrus juices wherein bitterness is due to limonin, the invention is equally applicable to reduce bitterness due to naringin. The bitterness of some citrus juices—for example, those derived from grapefruit, pummelos, or Seville oranges—is caused by the presence of naringin as well as limonin.

Despite the abundance of high-quality navel oranges each year, very little of the fruit is consumed in the form of unblended navel orange juice. This is due to the fact that the juice from navel oranges becomes bitter soon after it is extracted from the fruit.

Various methods have been advocated to remove the bitterness from the juice or to prevent its formation. Early investigators observe that juice from late-season navel oranges tended to have less bitterness than juice from early-season fruit. Unfortunately, the low bitterness levels were reached very late in the harvest season, after most of the crop had been harvested. Other investigators attempted to simulate this natural debittering process by storing early-season navel oranges in warm, moist rooms. Although some debittering was achieved during prolonged storage, this approach had a number of serious drawbacks which prevented its commercialization. These disadvantages included the growth of molds and other microorganisms, the large amount of time required, the development of off-flavors, and the necessity for special storage rooms.

An object of the present invention is to obviate the problems outlined above. In accordance with the invention, the bitterness in navel orange juice (or other citrus juice) is reduced by adding thereto a minor proportion of neodiosmin. The primary advantages of the invention are its effectiveness coupled with its simplicity in that the sole processing required is to mix the neodiosmin with the juice.

The compound primarily responsible for bitterness in navel orange juice is limonin. Because of its intense bitterness, only a very small amount of limonin is needed to render the juice unpalatable. Limonin is produced, after the juice is extracted, in a manner represented by the following scheme:

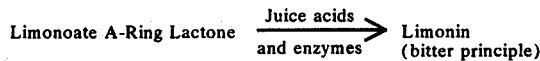

The non-bitter substance, limonoate A-ring lactone (hereinafter referred to as LARL), occurs naturally in the fruit tissues where it is stable and remains non-bitter. However, when the fruit tissues are ruptured, as in juice extraction, this normally non-bitter substance is attacked by the juice enzymes and is converted into limonin.

It may be noted that if the oranges are eaten as whole fruit, this bitterness will not be encountered. This is true because a certain amount of time is required for the chemical conversion of LARL into limonin by the fruit enzymes released during tissue disruption. Thus, if the orange is eaten in its fresh, whole state, there is not enough time for the generation of the bitter principle. However, as soon as the whole fruit is processed in order to extract a juice therefrom, the formation of limonin begins. This increase in limonin concentration continues until all of the LARL is converted to limonin.

As mentioned earlier, limonin is intensely bitter and only a small amount is necessary to render the juice bitter. Although the sensitivity to limonin among individuals varies, generally a majority of persons will perceive bitterness in orange juice when the limonin concentration is about 5 ppm, and will consider an orange juice to be unpalatable when its limonin concentration is about 10 ppm or higher. We have found that when neodiosmin is added to orange juice, a greater amount of limonin is necessary in order to render the juice bitter. In other words, a higher concentration of limonin is necessary before an individual can preceive a bitter taste in juice containing neodiosmin as compared with a juice that does not contain neodiosmin. It is to be emphasized that neodiosmin operates by suppressing the perception of bitterness. Thus when neodiosmin is added to orange juice containing a certain amount of limonin, the juice will taste less bitter than the same juice to which neodiosmin has not been added. Unlike prior methods for reducing bitterness in orange juice, the invention does not involve chemical alteration of limonin or of the limonin precursor. Also, as noted hereinabove, neodiosmin operates by suppressing the perception of bitterness due to the presence of naringin. It is further to be observed that neodiosmin does not operate by any masking action, because neodiosmin itself is tasteless and odorless.

The amount of neodiosmin to be added to the juice will depend on various factors such as the kind of juice, the concentration of limonin (or naringin) therein, and the degree of bitterness suppression desired. In any particular case, the proper amount of neodiosmin to be added can be readily determined by pilot trials. In any event, only a very minor amount of neodiosmin is needed. Thus in general, it has been found that useful results are obtained by adding about 50 to 150 ppm of neodiosmin based on the weight of the juice. The juice of reduced bitterness is prepared simply by dissolving the added neodiosmin in the juice.

Neodiosmin is a known compound. The synthesis thereof by oxidation of neohesperidin is disclosed by Horowitz and Gentili, Journal of Agricultural & Food Chemistry, Vol. 17, at page 698 (1969). The structure of neodiosmin is -

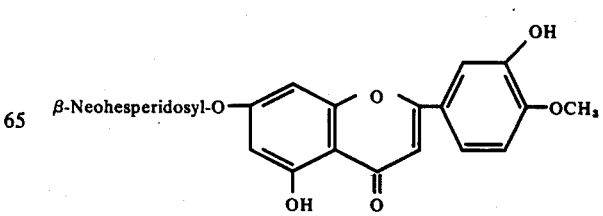

EXAMPLES

The invention is further demonstrated by the following illustrative examples.

EXAMPLE 1

Reduction of Bitterness Due to Limonin

A quantity of orange juice containing 10 ppm of limonin was procured, and divided into several lots.

Comparison A: To one lot of the juice was added 60 ppm of neodiosmin. A panel of 40 judges trained in food tasting was asked to taste 20-ml. samples of the juice with and without neodiosmin, and to indicate which of the samples was less bitter. The samples were known to the panel only by code numbers. The results were that 26 of the judges (65% of the panel) decided that the juice with added neodiosmin was less bitter than the control juice (no added neodiosmin).

Comparison B: The procedure of previous test was repeated except that in this case the 40-judge panel tasted samples of the juice with 100 ppm of neodiosmin and samples of the juice without neodiosmin. The results were that 30 the judges (75% of the panel) decided that the juice with added neodiosmin was less bitter than the control juice (no added neodiosmin).

EXAMPLE 2

Reduction of Bitterness Due to Naringin

The procedure employed in Example 1 was followed with the following changes: A sample of water containing 20 ppm of naringin was compared with a water sample containing 65 ppm of naringin and 10 ppm of neodiosmin. The results showed that neodiosmin suppressed naringin bitterness. In particular, 75% of the panel of judges decided that the sample containing 65 ppm of naringin and 10 ppm of neodiosmin was less bitter than the sample containing only 20 ppm of naringin.

Having thus described our invention, we claim:

1. A process for reducing bitterness in navel orange juice, said bitterness resulting from the presence of limonin in the juice, which comprises -
    adding to the juice neodiosmin in an amount sufficient to reduce the bitterness therein.
2. The process of claim 1 wherein the amount of added neodiosmin is 100 ppm.
3. A composition of matter, comprising -
    a. navel orange juice having a bitter taste resulting from the presence of limonin therein, and
    b. neodiosmin in an amount to reduce the bitterness of the juice.
4. The composition of claim 3 wherein the amount of neodiosmin is 100 ppm.

* * * * *